(12) United States Patent
Ikebe et al.

(10) Patent No.: US 9,364,400 B2
(45) Date of Patent: Jun. 14, 2016

(54) WATER-IN-OIL EMULSIFIED SUNSCREEN COSMETIC

(75) Inventors: Yosuke Ikebe, Yokohama (JP); Koji Abe, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 3 days.

(21) Appl. No.: 14/002,124

(22) PCT Filed: Aug. 9, 2012

(86) PCT No.: PCT/JP2012/070295
§ 371 (c)(1),
(2), (4) Date: Sep. 11, 2013

(87) PCT Pub. No.: WO2013/031510
PCT Pub. Date: Mar. 7, 2013

(65) Prior Publication Data
US 2013/0344013 A1    Dec. 26, 2013

(30) Foreign Application Priority Data

Aug. 31, 2011  (JP) .................................. 2011-188479
Aug. 6, 2012   (JP) .................................. 2012-173954

(51) Int. Cl.
| | | |
|---|---|---|
| A61Q 17/04 | (2006.01) | |
| A61K 8/06 | (2006.01) | |
| A61K 8/895 | (2006.01) | |
| A61K 8/81 | (2006.01) | |
| A61K 8/894 | (2006.01) | |
| A61K 8/02 | (2006.01) | |

(52) U.S. Cl.
CPC .............. *A61K 8/064* (2013.01); *A61K 8/0254* (2013.01); *A61K 8/8152* (2013.01); *A61K 8/894* (2013.01); *A61K 8/895* (2013.01); *A61Q 17/04* (2013.01); *A61K 2800/612* (2013.01)

(58) Field of Classification Search
CPC .................................. A61K 8/06; A61Q 17/04
See application file for complete search history.

(56) References Cited

U.S. PATENT DOCUMENTS

| | | | | |
|---|---|---|---|---|
| 6,936,241 | B2 * | 8/2005 | Yamada et al. | 424/59 |
| 2011/0104222 | A1 * | 5/2011 | Iida et al. | 424/401 |

FOREIGN PATENT DOCUMENTS

| | | |
|---|---|---|
| EP | 2 127 633 A1 | 12/2009 |
| EP | 2 216 296 A2 | 8/2010 |
| GB | 2326593 A | 12/1998 |
| JP | 2003-286150 A | 10/2003 |
| JP | 2005-314258 A | 11/2005 |
| JP | 2006-232740 A | 9/2006 |
| JP | 2007-182391 A | 7/2007 |
| JP | 2010-030971 A | 2/2010 |
| JP | 2010-159229 A | 7/2010 |
| JP | 2011-042589 A | 3/2011 |
| WO | 01/12152 A2 | 2/2001 |

OTHER PUBLICATIONS

The International Bureau of WIPO, "Notification of Transmittal of Translation of the International Preliminary Report on Patentability," issued in International Application No. PCT/JP2012/070295, of which U.S. Appl. No. 14/002,124 is a U.S. national phase entry, with a date of mailing of Mar. 13, 2014.
The European Patent Office, "The Extended European Search Report," issued in European Application No. 12828531.9-1458 / 2692338, PCT/JP2012070295, which is a European counterpart application to U.S. Appl. No. 14/002,124, with a date of notification of Aug. 1, 2014.
European Patent Office, Office Action, issued in EP Application No. 12 828 531.9, which is a European counterpart of U.S. Appl. No. 14/002,124, with an issuance date of Feb. 9, 2015, 4 pages.

* cited by examiner

*Primary Examiner* — Nannette Holloman

(57) ABSTRACT

The present invention provides a water-in-oil emulsified sunscreen cosmetic characteristically comprising the following (a) through (g):
(a) Ultraviolet absorbent
(b) Silicone backbone powder
(c) Methyl polymethacrylate powder
(d) Hydrophobicized platelike powder
(e) Surfactant
(f) Oil component
(g) Water The object of the present invention is to provide a water-in-oil emulsified sunscreen cosmetic that manifests a superior texture during use, a high ultraviolet protection effect, and superior stability.

6 Claims, No Drawings

WATER-IN-OIL EMULSIFIED SUNSCREEN COSMETIC

CROSS-REFERENCE TO RELATED APPLICATIONS

This patent application is a U.S. national stage application under 35 U.S.C. §371 of International Patent Application No. PCT/JP2012/070295 filed on Aug. 9, 2012, which claims the benefit of foreign priority to Japanese Patent Application No. JP 2011-188479 filed on Aug. 31, 2011, and to Japanese Patent Application No. JP 2012-173954 filed on Aug. 6, 2012, the disclosures of all of which are hereby incorporated by reference in their entireties. The International Application was published in Japanese on Mar. 7, 2013, as International Publication No. WO 2013/031510 A1 under PCT Article 21(2).

TECHNICAL FIELD

The present invention relates to a water-in-oil emulsified sunscreen cosmetic. More specifically, it relates to a water-in-oil emulsified sunscreen cosmetic that manifests a superior texture during use, a high ultraviolet protection effect, and superior stability by having specific powders blended in.

BACKGROUND ART

Patent Document 1 discloses a water-in-oil emulsified sunscreen cosmetic that has the effect of improving the ultraviolet protection. However, in said invention, it was necessary to blend in a water soluble polymer to increase the effect of improving the ultraviolet protection.

Patent Documents 2-5 disclose a sunscreen cosmetic containing a water soluble ultraviolet absorbent that is a water based composition or oil-in-water emulsified composition cosmetic wherein the SPF was increased while achieving superior usability, such as a dewy fresh texture. However, since it was an invention that increases the SPF of phenylbenzimidazolesulfonic acid, which is a water soluble ultraviolet absorbent, a specific neutralizer that neutralizes phenylbenzimidazolesulfonic acid was necessary. Also, since it is a water based composition or oil-in-water emulsified composition cosmetic, there was the shortcoming of inferior long-lasting coverage compared with water-in-oil emulsified sunscreen cosmetics.

Patent Document 6 discloses water soluble sunscreen cosmetics and oil-in-water emulsified sunscreen cosmetics that achieve a high SPF by effectively blending in a water soluble ultraviolet absorbent. However, the means to secure a high SPF value required the addition of agar microgel. Also, since it is a water soluble sunscreen cosmetic or oil-in-water emulsified composition cosmetic, there was the shortcoming of inferior long-lasting coverage compared with water-in-oil emulsified sunscreen cosmetics.

Patent Document 7 discloses an oil-in-water emulsified cosmetic that can achieve a high SPF without the high blend ratio of an oil soluble ultraviolet absorbent or stickiness. Since said invention achieved a high SPF by blending in a specific amount of a constitutional pigment and/or silicone resin and higher alcohol, it required a constitutional pigment and/or silicone resin and higher alcohol, and there was the shortcoming of inferior long-lasting coverage compared with water-in-oil emulsified sunscreen cosmetics because it was an oil-in-water emulsified cosmetic.

PRIOR ART DOCUMENTS

Patent Documents

Patent Document 1: JP 2010-195773 A
Patent Document 2: JP 2011-111444 A
Patent Document 3: JP 2011-111445 A
Patent Document 4: JP 2011-111446 A
Patent Document 5: JP 2011-111447 A
Patent Document 6: JP 2011-51922 A
Patent Document 7: JP 2010-189281 A

DISCLOSURE OF INVENTION

Technical Problem

In view of the aforementioned problems, the inventors conducted earnest research on water-in-oil emulsified sunscreen cosmetics to improve the ultraviolet protection effect and discovered that the addition of a plurality of specific powders would enable an improvement in the ultraviolet protection effect and provide a water-in-oil emulsified sunscreen cosmetic that, despite being a water-in-oil emulsified sunscreen cosmetic, manifested superior texture during use, i.e., an absence of oiliness, a smooth sensation, and an absence of stickiness, as well as superior stability, thus completing the present invention.

The object of the present invention is to provide a water-in-oil emulsified sunscreen cosmetic that manifests a high ultraviolet protection effect due to the improvement in the ultraviolet protection effect, and despite being a water-in-oil emulsified sunscreen cosmetic, manifests superior texture during use, i.e., an absence of oiliness, a smooth sensation, and an absence of stickiness, as well as superior stability.

Technical Solution

That is, the invention provides a water-in-oil emulsified sunscreen cosmetic characteristically comprising the following (a) through (g):
(a) Ultraviolet absorbent
(b) Silicone backbone powder
(c) Methyl polymethacrylate powder
(d) Hydrophobicized platelike powder
(e) Surfactant
(f) Oil component
(g) Water Also, the present invention provides the aforementioned water-in-oil emulsified sunscreen cosmetic wherein said (a) ultraviolet absorbent is one, two or more selected from a group consisting of ethylhexyl methoxycinnamate, octocrylene, polysilicone-15, t-butylmethoxydibenzoylmethane, ethylhexyl triazone, diethylaminohydroxybenzoyl hexyl benzoate, bis ethylhexyloxyphenol methoxyphenyl triazine, oxybenzone-3, methylene bis benzotriazolyl tetramethylbutylphenol, phenylbenzimidazole sulfonic acid, homosalate, and ethylhexyl salicylate.

Furthermore, the present invention provides the aforementioned water-in-oil emulsified sunscreen cosmetic wherein said (b) silicone backbone powder is one, two or more selected from a group consisting of (vinyl dimethicone/methicone silsesquioxane) crosspolymer, polymethylsilsesquioxane, and (dimethicone/vinyl dimethicone) crosspolymer.

Also, the present invention provides the water-in-oil emulsified sunscreen cosmetic wherein said (d) hydrophobicized platelike powder is platelike powder coated with a surface treatment agent whose backbone is composed of silicone.

Furthermore, the present invention provides the water-in-oil emulsified sunscreen cosmetic wherein the blend ratio of each of said (b) silicone backbone powder, said (c) methyl polymethacrylate powder, and (d) hydrophobicized platelike powder is 0.01-9 wt % relative to the total amount of the water-in-oil emulsified sunscreen cosmetic.

Advantageous Effects of the Invention

The water-in-oil emulsified sunscreen cosmetic of the present invention, by blending in a plurality of specific powders, manifests a high ultraviolet protection effect due to the improvement in the ultraviolet protection effect, and, despite being a water-in-oil emulsified sunscreen cosmetic, manifests superior texture during use, i.e., an absence of oiliness, a smooth sensation, and an absence of stickiness, as well as superior stability.

BEST MODE FOR CARRYING OUT THE INVENTION

The present invention is described in detail below.

"(a) Ultraviolet Absorbent"

Selection of the ultraviolet absorbent for use in the present invention is not limited in particular as long as it can be blended into cosmetics; it is preferable to use one, two or more selected from a group consisting of ethylhexyl methoxycinnamate, octocrylene, polysilicone-15, t-butylmethoxydibenzoylmethane, ethylhexyl triazone, diethylaminohydroxybenzoyl hexyl benzoate, bis ethylhexyloxyphenol methoxyphenyl triazine, oxybenzone-3, methylene bis benzotriazolyl tetramethylbutylphenol, phenylbenzimidazole sulfonic acid, homosalate, and ethylhexyl salicylate.

The blend ratio of the ultraviolet absorbent is usually 3-35 wt %, preferably 3-30 wt %, more preferably 5-25 wt %, relative to the total amount of the water-in-oil emulsified sunscreen cosmetic.

"(b) Silicone Backbone Powder"

Selection of the silicone backbone powder is not limited in particular as long as it is a polymer powder having a silicone polymer as a backbone; it is preferable to use one, two or more spherical powders selected from a group consisting of (vinyl dimethicone/methicone silsesquioxane) crosspolymer, polymethylsilsesquioxane, and (dimethicone/vinyl dimethicone) crosspolymer.

It is particularly preferable to use (vinyl dimethicone/methicone silsesquioxane) crosspolymer and polymethylsilsesquioxane.

The average particle size of the powder is preferably 1-15 micrometers. The average particle size is determined by values obtained from visual observation of electron microscope pictures or from a particle size distribution measurement apparatus such as MICROTRAC 9320-HRC (from Microtrac Inc.).

A preferable blend ratio of the silicone backbone powder is 0.01-9 wt %, more preferably 0.1-6 wt %, relative to the total amount of the water-in-oil emulsified sunscreen cosmetic.

"(c) Methyl Polymethacrylate Powder"

The average particle size of the powder used in the present invention is preferably 3-15 micrometers. The average particle size is determined by values obtained from visual observation of electron microscope pictures or from a particle size distribution measurement apparatus such as MICROTRAC 9320-HRC (from Microtrac Inc.).

The blend ratio of the methyl polymethacrylate powder is usually 0.01-9 wt %, preferably 0.1-6 wt %, more preferably 0.1-3 wt %, relative to the total amount of the water-in-oil emulsified sunscreen cosmetic.

"(d) Hydrophobicized Platelike Powder"

The hydrophobicized platelike powder used in the present invention is preferably platelike powder hydrophobicized with a silicone hydrophobicizing agent. The selection is not limited in particular as long as it is platelike powder; examples include talc, sericite, and kaolin; and it is particularly preferable to use platelike talc powder hydrophobicized with dimethylpolysiloxane.

Regarding the size of the platelike talc powder, talc having an average particle size as measured by laser scattering of 5-30 micrometers that is usually blended into powder cosmetics can be used.

The blend ratio of the hydrophobicized platelike powder is usually 0.01-9 wt %, preferably 0.1-6 wt %, more preferably 0.1-3 wt %, relative to the total amount of the water-in-oil emulsified sunscreen cosmetic.

"(e) Surfactant"

The selection is not limited in particular as long as it is a surfactant that can be a constituent of a water-in-oil emulsified sunscreen cosmetic; preferable are silicone surfactants. A preferable silicone surfactant is a nonionic surfactant wherein the hydrophobic group is dimethylpolysiloxane and the hydrophilic group is polyoxyalkylene mono glycol ether (polyether). There are a structure in which polyether is grafted like a pendant onto dimethylsiloxane and also block copolymers. Examples include dimethylpolysiloxane polyethylene glycol, dimethylpolysiloxane/(polyoxyethylene/polyoxypropylene) copolymer, and polyoxyethylene/methylpolysiloxane copolymer.

In the present invention, commercial products such as Silicone KF-6017, Silicone KF-6028, Silicone KF-6038 (Shin-Etsu Chemical Co., Ltd.), which are polyoxyethylene-modified organopolysiloxane, can be used preferably.

The blend ratio of the surfactant is usually 0.1-6.0 wt %, preferably 0.5-6.0 wt %, more preferably 0.5-4.0 wt %, relative to the total amount of the water-in-oil emulsified sunscreen cosmetic.

"(f) Oil Component"

The oil component used in the present invention is an oil component that constitutes the oil phase of the water-in-oil emulsified sunscreen cosmetic. The selection is not limited in particular as long as it is an oil component usually used in water-in-oil emulsified sunscreen cosmetics; hydrocarbon oils, liquid fats and oils, solid fats and oils, waxes, higher fatty acids, higher alcohols, ester oils, silicone oils, etc. can be blended in as appropriate.

The blend ratio of the oil component (not including the ultraviolet absorbent) is usually 3.0-50.0 wt %, preferably 3.0-45.0 wt %, more preferably 5.0-45.0 wt %, relative to the total amount of the water-in-oil emulsified sunscreen cosmetic.

"(g) Water"

Water used in the present invention is an ingredient that constitutes the water phase of the water-in-oil emulsified sunscreen cosmetic.

In the water-in-oil emulsified sunscreen cosmetic of the present invention, the mass ratio of the water phase (including water soluble ingredients dissolved in water) and the oil phase (including ingredients dissolved or dispersed in the oil component) is preferably in the range of (water phase):(oil phase)=1:9-5:5.

The blend ratio of water is decided as appropriate for the product.

In addition to the aforementioned essential ingredients, other ingredients usually used in cosmetics can be blended in as appropriate into the water-in-oil emulsified sunscreen cosmetic of the present invention as long as the effect of the present invention is not adversely affected, and the cosmetic can be prepared with a conventional method; examples of such ingredients include humectants, thickeners, powders, alcohols, natural polymers, synthetic polymers, sugars, antioxidants, buffers, various extracts, stabilizers, preservatives, pigments, and perfumes.

EXAMPLES

The invention is described in detail through Examples below, but the invention shall not be limited to them. The blend ratios in the recipes are in relation to the total amount and in mass-percentage units unless specified otherwise.

Using the formulations shown in "Table 1" through "Table 5", a conventional method was used to prepare water-in-oil emulsified sunscreen cosmetics (emulsion sun care cosmetics) and the texture during use, the improvement in the ultraviolet protection effect, and stability were evaluated.

"Texture During Use: Absence of Oiliness"

An actual use test with a panel of ten specialists (the sunscreen cosmetics of Examples and Comparative examples were applied on the upper arm) was conducted to evaluate the absence of oiliness.

<Evaluation Criteria>
⊚: 7 or more of the 10 reported they did not feel the oiliness.
○: 5 or more and less than 7 of the 10 reported they did not feel the oiliness.
Δ: 3 or more and less than 5 of the 10 reported they did not feel the oiliness.
X: 2 or less of the 10 reported they did not feel the oiliness.

"Texture During Use: Smooth Sensation"

An actual use test with a panel of ten specialists (the sunscreen cosmetics of Examples and Comparative examples were applied on the upper arm) was conducted to evaluate the smooth sensation.

<Evaluation Criteria>
⊚: 7 or more of the 10 reported there was a smooth sensation.
○: 5 or more and less than 7 of the 10 reported there was a smooth sensation.
Δ: 3 or more and less than 5 of the 10 reported there was a smooth sensation.
X: 2 or less of the 10 reported there was a smooth sensation.

"Texture During Use: Absence of Stickiness"

An actual use test with a panel of ten specialists (the sunscreen cosmetics of Examples and Comparative examples were applied on the upper arm) was conducted to evaluate the absence of stickiness.

<Evaluation Criteria>
⊚: 7 or more of the 10 reported they did not feel the stickiness.
○: 5 or more and less than 7 of the 10 reported they did not feel the stickiness.
Δ: 3 or more and less than 5 of the 10 reported they did not feel the stickiness.
X: 2 or less of the 10 reported they did not feel the stickiness.

"Improvement in the Ultraviolet Protection Effect"

For the ultraviolet protection effect, a spectrophotometer (U-4100 from Hitachi High-Technologies Corporation) was used to determine the absorbance integral value at 290-400 nm and the effect was expressed by the rate of increase from the absorbance integral value of Comparative example 1, using Comparative example 1 (powder ingredients b, c, and d were not blended in) as the control. For example, if the absorbance integral value of Comparative example 1 is 100, the absorbance integral value of Example 1 is 157, indicating a 57 point improvement in the ultraviolet protection effect.

For the substrate, a sand blast device PNEUMA BLASTER (from Fuji Manufacturing) was used to blast FUJI WHITE ALUMINA WA (from Fuji Manufacturing), particle size #16, onto one side of Acrylite 000 (from Mitsubishi Rayon Co., Ltd.) for a sandblast treatment, followed by cutting into 50 mm squares, and a skin substitute film was used. (The substrate used in the present invention is the same as the substrate used in U.S. Pat. No. 4,454,695.)

The sunscreen cosmetics of Comparative examples and Examples were applied and spread with a finger wearing a finger sack on the skin substitute film to the thickness of 2.00 mg/cm$^2$; the spectrophotometer was used to measure the absorbance at 290-400 nm and the integral value was determined.

Three skin substitute film substrates coated with the sunscreen cosmetics of Comparative examples and Examples were measured; for each substrate, five points were measured, i.e., near the center and near midpoints between the center and four corners, and the absorbance integral value was determined from their average.

"Stability"

The emulsion was put into a sample tube(s) right after preparation, and visual observation after leaving it alone at 50° C. for one month and a powder aggregation acceleration test were conducted.

<Evaluation Criteria>
○: The oil phase and the water phase are completely miscible with each other and powder is homogeneously dispersed.
Δ: The oil phase and the water phase are partially separated and powder is homogeneously dispersed.
X: The oil phase and the water phase are partially separated and powder is significantly aggregated.

TABLE 1

| Classification | Ingredient name | Comparative example 1 | Comparative example 2 | Comparative example 3 | Comparative example 4 | Comparative example 5 | Comparative example 6 | Comparative example 7 |
| --- | --- | --- | --- | --- | --- | --- | --- | --- |
| (g) Water | Water | Balance | Balance | Balance | Balance | Balance | Balance | Balance |
| Alcohol | Ethanol | 10 | 10 | 10 | 10 | 10 | 10 | 10 |
| Humectant | Glycerin | 1 | 1 | 1 | 1 | 1 | 1 | 1 |
|  | Xylitol | 1 | 1 | 1 | 1 | 1 | 1 | 1 |
| (e) Surfactant | PEG-9 polydimethylsiloxyethyl dimethicone | 1 | 1 | 1 | 1 | 1 | 1 | 1 |
|  | Lauryl PEG-9 polydimethylsiloxyethyl dimethicone | 1 | 1 | 1 | 1 | 1 | 1 | 1 |
| Chelating agent | EDTA-3Na | 0.1 | 0.1 | 0.1 | 0.1 | 0.1 | 0.1 | 0.1 |
| Thickener | Disteardimonium hectorite | 0.5 | 0.5 | 0.5 | 0.5 | 0.5 | 0.5 | 0.5 |
| (f) Oil component | Isododecane | 12.5 | 12.5 | 12.5 | 12.5 | 12.5 | 12.5 | 12.5 |
|  | Diisopropyl sebacate | 10 | 10 | 10 | 10 | 10 | 10 | 10 |
|  | Triethylhexanoin | 3 | 3 | 3 | 3 | 3 | 3 | 3 |

TABLE 1-continued

| Classification | Ingredient name | Comparative example 1 | Comparative example 2 | Comparative example 3 | Comparative example 4 | Comparative example 5 | Comparative example 6 | Comparative example 7 |
|---|---|---|---|---|---|---|---|---|
| | Cetyl ethylhexanoate | 3 | 3 | 3 | 3 | 3 | 3 | 3 |
| | Ethylhexyl palmitate | 5 | 5 | 5 | 5 | 5 | 5 | 5 |
| | Isopropyl myristate | 5 | 5 | 5 | 5 | 5 | 5 | 5 |
| Coating agent | Trimethylsiloxysilicic acid | 2 | 2 | 2 | 2 | 2 | 2 | 2 |
| (a) Ultraviolet absorbent | Ethylhexyl methoxycinnamate | 7.5 | 7.5 | 7.5 | 7.5 | 7.5 | 7.5 | 7.5 |
| | Octocrylene | 5 | 5 | 5 | 5 | 5 | 5 | 5 |
| | Polysilicone-15 | 5 | 5 | 5 | 5 | 5 | 5 | 5 |
| | Ethylhexyl triazone | 1 | 1 | 1 | 1 | 1 | 1 | 1 |
| | Oxybenzone-3 | 1 | 1 | 1 | 1 | 1 | 1 | 1 |
| | t-butylmethoxydibenzoylmethane | 1 | 1 | 1 | 1 | 1 | 1 | 1 |
| | Bis ethylhexyloxyphenol methoxyphenyl triazine | 1 | 1 | 1 | 1 | 1 | 1 | 1 |
| | Hexyl diethylaminohydroxybenzoylbenzoate | 1 | 1 | 1 | 1 | 1 | 1 | 1 |
| (b) Silicone backbone powder | Polymethylsilsesquioxane | | 6 | 9 | 12 | | | |
| | (Vinyl dimethicone/methicone silsesquioxane) crosspolymer | | | | | 6 | 9 | 12 |
| (c) Methyl polymethacrylate powder | Methyl polymethacrylate | | | | | | | |
| (d) Hydrophobicized plate like powder | Dimethicone-treated talc | | | | | | | |
| | Total | 100 | 100 | 100 | 100 | 100 | 100 | 100 |
| Texture during use | Absence of oiliness | X | X | X | X | X | X | Δ |
| | Smooth sensation | X | X | X | X | Δ | ◯ | ◯ |
| | Absence of stickiness | X | Δ | ◯ | ◎ | Δ | ◯ | ◎ |
| | Improvement in the ultraviolet protection effect | 0 | 38 | 48 | 51 | 67 | 68 | 75 |
| | Stability | X | X | X | X | X | X | Δ |

TABLE 2

| Classification | Ingredient name | Comparative example 8 | Comparative example 9 | Comparative example 10 | Comparative example 11 | Comparative example 12 | Comparative example 13 | Comparative example 14 |
|---|---|---|---|---|---|---|---|---|
| (g) Water | Water | Balance | Balance | Balance | Balance | Balance | Balance | Balance |
| Alcohol | Ethanol | 10 | 10 | 10 | 10 | 10 | 10 | 10 |
| Humectant | Glycerin | 1 | 1 | 1 | 1 | 1 | 1 | 1 |
| | Xylitol | 1 | 1 | 1 | 1 | 1 | 1 | 1 |
| (e) Surfactant | PEG-9 polydimethylsiloxyethyl dimethicone | 1 | 1 | 1 | 1 | 1 | 1 | 1 |
| | Lauryl PEG-9 polydimethylsiloxyethyl dimethicone | 1 | 1 | 1 | 1 | 1 | 1 | 1 |
| Chelating agent | EDTA-3Na | 0.1 | 0.1 | 0.1 | 0.1 | 0.1 | 0.1 | 0.1 |
| Thickener | Disteardimonium hectorite | 0.5 | 0.5 | 0.5 | 0.5 | 0.5 | 0.5 | 0.5 |
| (f) Oil component | Isododecane | 12.5 | 12.5 | 12.5 | 12.5 | 12.5 | 12.5 | 12.5 |
| | Diisopropyl sebacate | 10 | 10 | 10 | 10 | 10 | 10 | 10 |
| | Triethylhexanoin | 3 | 3 | 3 | 3 | 3 | 3 | 3 |
| | Cetyl ethylhexanoate | 3 | 3 | 3 | 3 | 3 | 3 | 3 |
| | Ethylhexyl palmitate | 5 | 5 | 5 | 5 | 5 | 5 | 5 |
| | Isopropyl myristate | 5 | 5 | 5 | 5 | 5 | 5 | 5 |
| Coating agent | Trimethylsiloxysilicic acid | 2 | 2 | 2 | 2 | 2 | 2 | 2 |
| (a) Ultraviolet absorbent | Ethylhexyl methoxycinnamate | 7.5 | 7.5 | 7.5 | 7.5 | 7.5 | 7.5 | 7.5 |
| | Octocrylene | 5 | 5 | 5 | 5 | 5 | 5 | 5 |
| | Polysilicone-15 | 5 | 5 | 5 | 5 | 5 | 5 | 5 |
| | Ethylhexyl triazone | 1 | 1 | 1 | 1 | 1 | 1 | 1 |
| | Oxybenzone-3 | 1 | 1 | 1 | 1 | 1 | 1 | 1 |
| | t-butylmethoxydibenzoylmethane | 1 | 1 | 1 | 1 | 1 | 1 | 1 |
| | Bis ethylhexyloxyphenol methoxyphenyl triazine | 1 | 1 | 1 | 1 | 1 | 1 | 1 |
| | Hexyl diethylaminohydroxybenzoylbenzoate | 1 | 1 | 1 | 1 | 1 | 1 | 1 |

TABLE 2-continued

| Classification | Ingredient name | Comparative example 8 | Comparative example 9 | Comparative example 10 | Comparative example 11 | Comparative example 12 | Comparative example 13 | Comparative example 14 |
|---|---|---|---|---|---|---|---|---|
| (b) Silicone backbone powder | Polymethylsilsesquioxane | | | | | | | 6 |
| | (Vinyl dimethicone/methicone silsesquioxane) crosspolymer | | | | | | | 6 |
| (c) Methyl polymethacrylate powder | Methyl polymethacrylate | 6 | 9 | 12 | | | | |
| (d) Hydrophobicized plate like powder | Dimethicone-treated talc | | | | 6 | 9 | 12 | |
| | Total | 100 | 100 | 100 | 100 | 100 | 100 | 100 |
| Texture during use | Absence of oiliness | △ | ○ | ◎ | ○ | ○ | ○ | X |
| | Smooth sensation | ○ | ◎ | ◎ | X | X | △ | ○ |
| | Absence of stickiness | ○ | ◎ | ◎ | X | X | △ | ◎ |
| | Improvement in the ultraviolet protection effect | 42 | 42 | 73 | 21 | 43 | 49 | 71 |
| | Stability | X | X | X | X | X | X | △ |

TABLE 3

| Classification | Ingredient name | Comparative example 15 | Comparative example 16 | Comparative example 17 | Comparative example 18 | Comparative example 19 | Example 1 | Example 2 |
|---|---|---|---|---|---|---|---|---|
| (g) Water | Water | Balance | Balance | Balance | Balance | Balance | Balance | Balance |
| Alcohol | Ethanol | 10 | 10 | 10 | 10 | 10 | 10 | 10 |
| Humectant | Glycerin | 1 | 1 | 1 | 1 | 1 | 1 | 1 |
| | Xylitol | 1 | 1 | 1 | 1 | 1 | 1 | 1 |
| (e) Surfactant | PEG-9 polydimethylsiloxyethyl dimethicone | 1 | 1 | 1 | 1 | 1 | 1 | 1 |
| | Lauryl PEG-9 polydimethylsiloxyethyl dimethicone | 1 | 1 | 1 | 1 | 1 | 1 | 1 |
| Chelating agent | EDTA-3Na | 0.1 | 0.1 | 0.1 | 0.1 | 0.1 | 0.1 | 0.1 |
| Thickener | Disteardimonium hectorite | 0.5 | 0.5 | 0.5 | 0.5 | 0.5 | 0.5 | 0.5 |
| (f) Oil component | Isododecane | 12.5 | 12.5 | 12.5 | 12.5 | 12.5 | 12.5 | 12.5 |
| | Diisopropyl sebacate | 10 | 10 | 10 | 10 | 10 | 10 | 10 |
| | Triethylhexanoin | 3 | 3 | 3 | 3 | 3 | 3 | 3 |
| | Cetyl ethylhexanoate | 3 | 3 | 3 | 3 | 3 | 3 | 3 |
| | Ethylhexyl palmitate | 5 | 5 | 5 | 5 | 5 | 5 | 5 |
| | Isopropyl myristate | 5 | 5 | 5 | 5 | 5 | 5 | 5 |
| Coating agent | Trimethylsiloxysilicic acid | 2 | 2 | 2 | 2 | 2 | 2 | 2 |
| (a) Ultraviolet absorbent | Ethylhexyl methoxycinnamate | 7.5 | 7.5 | 7.5 | 7.5 | 7.5 | 7.5 | 7.5 |
| | Octocrylene | 5 | 5 | 5 | 5 | 5 | 5 | 5 |
| | Polysilicone-15 | 5 | 5 | 5 | 5 | 5 | 5 | 5 |
| | Ethylhexyl triazone | 1 | 1 | 1 | 1 | 1 | 1 | 1 |
| | Oxybenzone-3 | 1 | 1 | 1 | 1 | 1 | 1 | 1 |
| | t-butylmethoxydibenzoylmethane | 1 | 1 | 1 | 1 | 1 | 1 | 1 |
| | Bis ethylhexyloxyphenol methoxyphenyl triazine | 1 | 1 | 1 | 1 | 1 | 1 | 1 |
| | Hexyl diethylaminohydroxybenzoylbenzoate | 1 | 1 | 1 | 1 | 1 | 1 | 1 |
| (b) Silicone backbone powder | Polymethylsilsesquioxane | 6 | 6 | | | | 3 | 3 |
| | (Vinyl dimethicone/methicone silsesquioxane) crosspolymer | | | 6 | 6 | | 3 | |
| (c) Methyl polymethacrylate powder | Methyl polymethacrylate | 6 | | 6 | | 6 | 3 | 3 |
| (d) Hydrophobicized plate like powder | Dimethicone-treated talc | | 6 | | 6 | 6 | 3 | 0.1 |
| | Total | 100 | 100 | 100 | 100 | 100 | 100 | 100 |
| Texture during use | Absence of oiliness | △ | ○ | △ | ○ | ○ | ◎ | ○ |
| | Smooth sensation | ○ | △ | ○ | △ | ○ | ◎ | ○ |
| | Absence of stickiness | ○ | △ | ○ | X | ○ | ◎ | ◎ |
| | Improvement in the ultraviolet protection effect | 54 | 55 | 74 | 75 | 65 | 57 | 37 |
| | Stability | X | △ | △ | △ | △ | ○ | ○ |

TABLE 4

| Classification | Ingredient name | Example 3 | Example 4 | Example 5 | Example 6 | Example 7 | Example 8 | Example 9 |
|---|---|---|---|---|---|---|---|---|
| (g) Water | Water | Balance | Balance | Balance | Balance | Balance | Balance | Balance |
| Alcohol | Ethanol | 10 | 10 | 10 | 10 | 10 | 10 | 10 |
| Humectant | Glycerin | 1 | 1 | 1 | 1 | 1 | 1 | 1 |
|  | Xylitol | 1 | 1 | 1 | 1 | 1 | 1 | 1 |
| (e) Surfactant | PEG-9 polydimethylsiloxyethyl dimethicone | 1 | 1 | 1 | 1 | 1 | 1 | 1 |
|  | Lauryl PEG-9 polydimethylsiloxyethyl dimethicone | 1 | 1 | 1 | 1 | 1 | 1 | 1 |
| Chelating agent | EDTA-3Na | 0.1 | 0.1 | 0.1 | 0.1 | 0.1 | 0.1 | 0.1 |
| Thickener | Disteardimonium hectorite | 0.5 | 0.5 | 0.5 | 0.5 | 0.5 | 0.5 | 0.5 |
| (f) Oil component | Isododecane | 12.5 | 12.5 | 12.5 | 12.5 | 12.5 | 12.5 | 12.5 |
|  | Diisopropyl sebacate | 10 | 10 | 10 | 10 | 10 | 10 | 10 |
|  | Triethylhexanoin | 3 | 3 | 3 | 3 | 3 | 3 | 3 |
|  | Cetyl ethylhexanoate | 3 | 3 | 3 | 3 | 3 | 3 | 3 |
|  | Ethylhexyl palmitate | 5 | 5 | 5 | 5 | 5 | 5 | 5 |
|  | Isopropyl myristate | 5 | 5 | 5 | 5 | 5 | 5 | 5 |
| Coating agent | Trimethylsiloxysilicic acid | 2 | 2 | 2 | 2 | 2 | 2 | 2 |
| (a) Ultraviolet absorbent | Ethylhexyl methoxycinnamate | 7.5 | 7.5 | 7.5 | 7.5 | 7.5 | 7.5 | 7.5 |
|  | Octocrylene | 5 | 5 | 5 | 5 | 5 | 5 | 5 |
|  | Polysilicone-15 | 5 | 5 | 5 | 5 | 5 | 5 | 5 |
|  | Ethylhexyl triazone | 1 | 1 | 1 | 1 | 1 | 1 | 1 |
|  | Oxybenzone-3 | 1 | 1 | 1 | 1 | 1 | 1 | 1 |
|  | t-butylmethoxydibenzoylmethane | 1 | 1 | 1 | 1 | 1 | 1 | 1 |
|  | Bis ethylhexyloxyphenol methoxyphenyl triazine | 1 | 1 | 1 | 1 | 1 | 1 | 1 |
|  | Hexyl diethylaminohydroxybenzoylbenzoate | 1 | 1 | 1 | 1 | 1 | 1 | 1 |
| (b) Silicone backbone powder | Polymethylsilsesquioxane (Vinyl dimethicone/methicone silsesquioxane) crosspolymer | 3 | 0.1 | 6 | 0.1 | 0.1 | 9 | 0.1 |
| (c) Methyl polymethacrylate powder | Methyl polymethacrylate | 0.1 | 3 | 0.1 | 6 | 0.1 | 0.1 | 9 |
| (d) Hydrophobicized plate like powder | Dimethicone-treated talc | 3 | 3 | 0.1 | 0.1 | 6 | 0.1 | 0.1 |
|  | Total | 100 | 100 | 100 | 100 | 100 | 100 | 100 |
| Texture during use | Absence of oiliness | ○ | ◎ | ○ | ○ | ○ | ○ | ○ |
|  | Smooth sensation | ○ | ○ | ○ | ○ | ○ | ○ | ◎ |
|  | Absence of stickiness | ◎ | ○ | ◎ | ○ | ○ | ◎ | ◎ |
| Improvement in the ultraviolet protection effect |  | 30 | 32 | 34 | 32 | 34 | 45 | 42 |
|  | Stability | ○ | ○ | ○ | ○ | ○ | ○ | ○ |

TABLE 5

| Classification | Ingredient name | Example 10 | Example 11 | Example 12 | Example 13 | Example 14 | Example 15 | Example 16 |
|---|---|---|---|---|---|---|---|---|
| (g) Water | Water | Balance | Balance | Balance | Balance | Balance | Balance | Balance |
| Alcohol | Ethanol | 10 | 10 | 10 | 10 | 10 | 10 | 10 |
| Humectant | Glycerin | 1 | 1 | 1 | 1 | 1 | 1 | 1 |
|  | Xylitol | 1 | 1 | 1 | 1 | 1 | 1 | 1 |
| (e) Surfactant | PEG-9 polydimethylsiloxyethyl dimethicone | 1 | 1 | 1 | 1 | 1 | 1 | 1 |
|  | Lauryl PEG-9 polydimethylsiloxyethyl dimethicone | 1 | 1 | 1 | 1 | 1 | 1 | 1 |
| Chelating agent | EDTA-3Na | 0.1 | 0.1 | 0.1 | 0.1 | 0.1 | 0.1 | 0.1 |
| Thickener | Disteardimonium hectorite | 0.5 | 0.5 | 0.5 | 0.5 | 0.5 | 0.5 | 0.5 |
| (f) Oil component | Isododecane | 12.5 | 12.5 | 12.5 | 12.5 | 12.5 | 12.5 | 12.5 |
|  | Diisopropyl sebacate | 10 | 10 | 10 | 10 | 10 | 10 | 10 |
|  | Triethylhexanoin | 3 | 3 | 3 | 3 | 3 | 3 | 3 |
|  | Cetyl ethylhexanoate | 3 | 3 | 3 | 3 | 3 | 3 | 3 |
|  | Ethylhexyl palmitate | 5 | 5 | 5 | 5 | 5 | 5 | 5 |
|  | Isopropyl myristate | 5 | 5 | 5 | 5 | 5 | 5 | 5 |
| Coating agent | Trimethylsiloxysilicic acid | 2 | 2 | 2 | 2 | 2 | 2 | 2 |
| (a) Ultraviolet absorbent | Ethylhexyl methoxycinnamate | 7.5 | 7.5 | 7.5 | 7.5 | 7.5 | 7.5 | 7.5 |
|  | Octocrylene | 5 | 5 | 5 | 5 | 5 | 5 | 5 |
|  | Polysilicone-15 | 5 | 5 | 5 | 5 | 5 | 5 | 5 |
|  | Ethylhexyl triazone | 1 | 1 | 1 | 1 | 1 | 1 | 1 |

TABLE 5-continued

| Classification | Ingredient name | Example 10 | Example 11 | Example 12 | Example 13 | Example 14 | Example 15 | Example 16 |
|---|---|---|---|---|---|---|---|---|
| | Oxybenzone-3 | 1 | 1 | 1 | 1 | 1 | 1 | 1 |
| | t-butylmethoxydibenzoylmethane | 1 | 1 | 1 | 1 | 1 | 1 | 1 |
| | Bis ethylhexyloxyphenol methoxyphenyl triazine | 1 | 1 | 1 | 1 | 1 | 1 | 1 |
| | Hexyl diethylaminohydroxybenzoylbenzoate | 1 | 1 | 1 | 1 | 1 | 1 | 1 |
| (b) Silicone backbone powder | Polymethylsilsesquioxane (Vinyl dimethicone/methicone silsesquioxane) crosspolymer | 0.1 | 6 | 6 | 0.1 | 12 | 0.1 | 0.1 |
| (c) Methyl polymethacrylate powder | Methyl polymethacrylate | 0.1 | 6 | 0.1 | 6 | 0.1 | 12 | 0.1 |
| (d) Hydrophobicized plate like powder | Dimethicone-treated talc | 9 | 0.1 | 6 | 6 | 0.1 | 0.1 | 12 |
| | Total | 100 | 100 | 100 | 100 | 100 | 100 | 100 |
| Texture during use | Absence of oiliness | ○ | ○ | ○ | ○ | ○ | ○ | ○ |
| | Smooth sensation | ○ | ◎ | ◎ | ◎ | ○ | ◎ | ○ |
| | Absence of stickiness | ○ | ◎ | ○ | ○ | ◎ | ◎ | ○ |
| Improvement in the ultraviolet protection effect | | 43 | 51 | 43 | 57 | 51 | 67 | 52 |
| | Stability | ○ | ○ | ○ | ○ | ○ | ○ | ○ |

Comparative examples 1-19 and Examples 1-16 in these tables are water-in-oil emulsified sunscreen cosmetics, all of which have the same ingredients except for the essential three ingredients of the present invention, i.e., (b) silicone backbone powder, (c) methyl polymethacrylate powder, and (d) hydrophobicized platelike powder.

Example 1, which contains all of (b) silicone backbone powder, (c) methyl polymethacrylate powder, and (d) hydrophobicized platelike powder, is the most superior on all the items for the texture during use. Also, there is an improvement in the ultraviolet protection effect by 57 points compared with Comparative example 1, which does not contain (b) silicone backbone powder, (c) methyl polymethacrylate powder, and (d) hydrophobicized platelike powder. Furthermore, regarding stability, surprisingly, a single powder addition cannot maintain stability but the stability improves by blending two or more selected powders; this effect applies also to Example 1. This indicates that Example 1 manifests superior effects for all the effects. That is, said effect is an effect completely unpredictable by those skilled in the art that is made possible by (b) silicone backbone powder, (c) methyl polymethacrylate powder, and (d) hydrophobicized platelike powder, which are essential ingredients of the present invention.

Also, the water-in-oil emulsified sunscreen cosmetics of Examples 1-16 are substantially transparent when applied on the skin, i.e., there is no problem of white haze, and manifest superior long lasting coverage against perspiration, swimming in pools, and sea bathing.

INDUSTRIAL APPLICABILITY

The present invention is a new and useful invention that can provide a water-in-oil emulsified sunscreen cosmetic that manifests a superior texture during use, a high ultraviolet protection effect, and superior stability by blending in, as essential ingredients, three specific powders commonly used in powder cosmetics and such.

Also, the present invention is a water-in-oil emulsified sunscreen that is substantially transparent when applied on the skin, i.e., there is no problem of white haze, and manifests superior long lasting coverage against perspiration, swimming in pools, and sea bathing.

The invention claimed is:
1. A water-in-oil emulsified sunscreen cosmetic comprising the following (a) through (g):
 (a) Ultraviolet absorbent
 (b) Silicone backbone powder
 (c) Methyl polymethacrylate powder
 (d) Hydrophobicized plate powder
 (e) Surfactant
 (f) Oil component
 (g) Water;
wherein:
 the blend ratio of said (b) silicone backbone powder is 0.1-12 wt % relative to the total amount of the water-in-oil emulsified sunscreen cosmetic;
 the blend ratio of said (c) methyl polymethacrylate powder is 0.1-12 wt % relative to the total amount of the water-in-oil emulsified sunscreen cosmetic;
 the blend ratio of said (d) hydrophobicized plate powder is 0.1-12 wt % relative to the total amount of the water-in-oil emulsified sunscreen cosmetic;
 said (a) ultraviolet absorbent is one, two or more selected from the group consisting of ethylhexyl methoxycinnamate, octocrylene, polysilicone-15, t-butylmethoxydibenzoylmethane, ethylhexyl triazone, diethylaminohydroxybenzoyl hexyl benzoate, bis ethylhexyloxyphenol methoxyphenyl triazine, oxybenzone-3, methylene bis benzotriazolyl tetramethylbutylphenol, phenylbenzimidazole sulfonic acid, homosalate, and ethylhexyl salicylate;
 said (b) silicone backbone powder is polymethylsilsesquioxane; and
 said (d) hydrophobicized plate powder is dimethicone-treated talc.

2. The water-in-oil emulsified sunscreen cosmetic of claim 1, wherein the dimethicone-treated talc powder has an average particle size of 5-30 micrometers.

3. The water-in-oil emulsified sunscreen cosmetic of claim 1, wherein the sum of the blend ratios of said (b) silicone backbone powder, said (c) methyl polymethacrylate powder, and said (d) hydrophobicized plate powder is 6.1-12.2 wt % relative to the total amount of the water-in-oil emulsified sunscreen cosmetic.

4. A water-in-oil emulsified sunscreen cosmetic comprising the following (a) through (g):
(a) Ultraviolet absorbent
(b) Silicone backbone powder
(c) Methyl polymethacrylate powder
(d) Hydrophobicized plate powder
(e) Surfactant
(f) Oil component
(g) Water;
wherein:
the blend ratio of said (b) silicone backbone powder is 0.1-6 wt % relative to the total amount of the water-in-oil emulsified sunscreen cosmetic;
the blend ratio of said (c) methyl polymethacrylate powder is 0.1-12 wt % relative to the total amount of the water-in-oil emulsified sunscreen cosmetic;
the blend ratio of said (d) hydrophobicized plate powder is 0.1-12 wt % relative to the total amount of the water-in-oil emulsified sunscreen cosmetic;
said (a) ultraviolet absorbent is one, two or more selected from the group consisting of ethylhexyl methoxycinnamate, octocrylene, polysilicone-15, t-butylmethoxydibenzoylmethane, ethylhexyl triazone, diethylaminohydroxybenzoyl hexyl benzoate, bis ethylhexyloxyphenol methoxyphenyl triazine, oxybenzone-3, methylene bis benzotriazolyl tetramethylbutylphenol, phenylbenzimidazole sulfonic acid, homosalate, and ethylhexyl salicylate;
said (b) silicone backbone powder is polymethylsilsesquioxane and (vinyl dimethicone/methicone silsesquioxane) crosspolymer; and
said (d) hydrophobicized plate powder is dimethicone-treated talc.

5. The water-in-oil emulsified sunscreen cosmetic of claim 4, wherein the dimethicone-treated talc powder has an average particle size of 5-30 micrometers.

6. The water-in-oil emulsified sunscreen cosmetic of claim 4, wherein the sum of the blend ratios of said (b) silicone backbone powder, said (c) methyl polymethacrylate powder, and said (d) hydrophobicized plate powder is 6.1-12.2 wt % relative to the total amount of the water-in-oil emulsified sunscreen cosmetic.

* * * * *